United States Patent [19]

Böhner et al.

[11] 4,311,513
[45] Jan. 19, 1982

[54] HERBICIDAL α-PHENOXYPROPIONYLAZOLES, COMPOSITIONS CONTAINING THEM, AND METHOD OF USE THEREOF

[75] Inventors: Beat Böhner, Binningen; Hermann Rempfler, Ettingen, both of Switzerland

[73] Assignee: Ciba-Geigy Corporation, Ardsley, N.Y.

[21] Appl. No.: 178,220

[22] Filed: Aug. 14, 1980

[30] Foreign Application Priority Data

Aug. 24, 1979 [CH] Switzerland .............. 7727/79

[51] Int. Cl.³ .............. A01N 43/50; A01N 43/56; A01N 43/66; C07D 401/12
[52] U.S. Cl. .............. 71/92; 546/276; 546/278; 546/279; 546/281; 548/253; 548/255; 548/262; 548/341; 548/378; 260/326.5J; 71/88
[58] Field of Search .............. 546/276, 278, 279; 71/92

[56] References Cited

U.S. PATENT DOCUMENTS 4,046,553  9/1977  Takahashi et al .............. 71/92
4,213,774  7/1980  Shurter et al. .............. 546/276

Primary Examiner—John M. Ford
Assistant Examiner—Jane T. Fan
Attorney, Agent, or Firm—Frederick H. Rabin

[57] ABSTRACT

Herbicidal α-(4-substituted) phenoxypropionylazoles of the formula

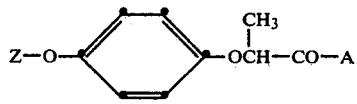

wherein Z is the 4-trifluoromethylphenyl, 3,5-dichloropyrid-(2)-yl or 3-chloro-5-trifluoromethyl-pyrid-(2)-yl radical, and A is an azole radical which may or may not be substituted and is bonded through a ring nitrogen atom, such as pyrazole, imidazole, triazole or tetrazole, are useful for selectively controlling monocotyledonous weeds. Preferably, the cultivated plants are dicotyledonous, such as wheat, cotton, sugar beet, soybeans and vegetables.

17 Claims, No Drawings

HERBICIDAL α-PHENOXYPROPIONYLAZOLES, COMPOSITIONS CONTAINING THEM, AND METHOD OF USE THEREOF

The present invention relates to novel α-phenoxypropionylazoles, the production thereof, compositions containing them, and a method of controlling undesired plant growth which comprises the use of these compounds and compositions.

The novel α-phenoxypropionyl-azoles have the formula I

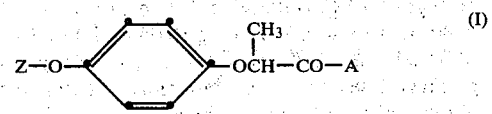

wherein Z is the 4-trifluoromethylphenyl, 3,5-dichloropyrid-(2)-yl or 3-chloro-5-trifluoromethyl-pyrid-(2)-yl radical, and A is an azole radical which is bonded through a ring nitrogen atom and which can be substituted by one or more of halogen, alkyl, alkoxy, alkylthio or perfluoroalkyl, each containing at most 4 carbon atoms, by cyano, carboxyl, and carbalkoxy containing at most 4 carbon atoms in the alkoxy moiety, or by $C_1$-$C_4$alkanoyl, and A can also denote salts of diazoles and triazoles. The preferred substituent is methyl.

The radicals Z have the following structure:

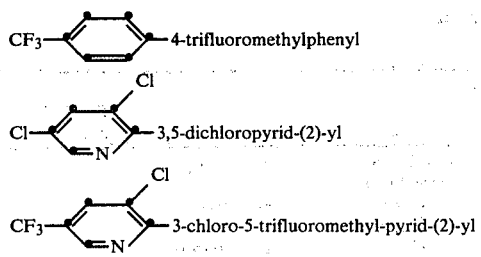

By azole radicals are meant unsubstituted or substituted aromatic, i.e. unsaturated, 5-membered heterocyclic ring systems containing 1 to 4 ring nitrogen atoms, such as pyrrole, imidazole, pyrazole, triazoles (1,2,3-, 1,2,4- and 1,3,4-triazoles), tetrazole. These azole radicals can be substituted by one or more of halogen, alkyl, alkoxy, alkylthio or perfluoroalkyl radicals (such as $CF_3$), each containing up to 4 carbon atoms, by cyano, carboxyl, and carbalkoxy radicals containing up to 4 carbon atoms in the alkoxy moiety, or by $C_1$-$C_4$alkanoyl, each independently of the other. Preferred azole radicals A in the molecule are: pyrazol-1-yl, 1,2,4-triazol-1-yl, imidazol-1-yl, and 3,5-dimethylpyrazol-1-yl.

Further examples of substituted azoles are: 2,6-dimethylpyrrole, tetramethylpyrrole, 3(5)-methylpyrazole, 4-methylpyrazole, 3(5)-ethylpyrazole, 4-ethylpyrazole, 3(5)-isopropylpyrazole, 4-isopropylpyrazole, 2,5-dimethyl-4-acetylpyrazole, 3,5-dimethyl-4-propionylpyrazole, 3,4,5-trimethylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bis-trifluoromethylpyrazole, 3(5)-methyl-5(3)-carbethoxypyrazole, 3,5-bis-carboethoxypyrazole, 3,4,5-tris-carboethoxypyrazole, 3(5)-methyl-5(3)-methylthio-4-carboethoxypyrazole, 4-methyl-3,5-bis-carboethoxypyrazole, 4-cyanopyrazole, 4-methoxy-3,5-dichloropyrazole, 3(5)-methyl-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3(5)-chloro-5(3)-cyano-1,2,4-triazole, 3(5)-chloro-5(3)-carbomethoxy-1,2,4-triazole, 3(5)-methylthio-1,2,4-triazole, 4(5)-methyl-1,2,3-triazole, 4,5-dimethyl-1,2,3-triazole, 4(5)-chloro-1,2,3-triazole, ethyl 1,2,3-triazol-4(5)-yl-carboxylate, dimethyl 1,2,3-triazol-4,5-yl-dicarboxylate, 5-methyltetrazole, 5-chlorotetrazole, ethyl tetrazolyl-5-carboxylate.

If the unsubstituted or substituted azole contains 2 or 3 nitrogen atoms, the radical A can also be linked in the form of a salt to one of the customary strong inorganic or organic acids such as hydrochloric acid, hydrobromic acid, nitric acid, sulfuric acid, tetrafluoroboric acid, fluorosulfonic acid, formic acid, a halogenated carboxylic acid, e.g. trichloroacetic acid, an alkanesulfonic acid, e.g. methanesulfonic acid, a halogenated alkanesulfonic acid, e.g. trifluoromethanesulfonic acid, perfluorohexanesulfonic acid, an arylsulfonic acid, e.g. dodecylbenzenesulfonic acid.

Herbicidal α-halopyridyl-(2)-oxy-phenoxypropionylamides, in which A is a saturated N-heterocyclic ring system or a triazole radical bonded through a —NH bridge, have already been disclosed in German Offenlegungsschrift No. 2 546 251 (compounds 57 and 71), and in U.S. Pat. No. 4,046,553. Compared with these and other prior art compounds, the compounds of the formula I have, surprisingly, a more potent herbicidal action, especially against monocotyledonous weeds in both preemergence and postemergence application. They are therefore most suitable for the selective control of monocotyledonous weeds in certain crops of dicotyledonous cultivated plants, e.g. soybeans and sugar beet, and also in crops of monocots such as wheat. Preferred compounds of the formula I are those wherein Z is the 3,5-dichloropyrid-(2)-yl radical and A is pyrazole, imidazole and 1,2,4-triazole. Compounds in which Z is the 3-chloro-5-trifluoromethyl-pyrid-(2)-yl radical are also very effective.

The compounds of the present invention have low toxicity to man and animals and no special precautionary measures are necessary for handling them. In the field they are advantageously employed in rates of application of 5 kg/ha and less. They can be used in preemergence application; but postemergence application is often preferred.

The novel α-phenoxypropionylazoles of the formula I can conveniently be obtained by reacting an appropriate propionyl halide, especially a chloride, of the formula

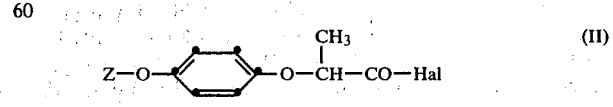

with a 1-trimethylsilylazole of the formula

in which formulae Z and A are as defined for formula I, to give the azole compound of the formula I with the formation of (CH₃)₃SiHal. This reaction is carried out in the temperature range from 0° to 100° C., preferably in an inert solvent such as diethyl ether, toluene, dioxane etc.

The starting α-phenoxypropionic acids of the formula II and their halides are known and described e.g. in the following publications: German Offenlegungsschrift No. 2 531 643 and 2 546 251, British patent specification No. 1 507 643, and U.S. Pat. No. 4,046,553. Various trimethylsilylazoles of the formula III, e.g. trimethylsilylpyrazole, trimethylsilyl-1,2,4-triazole and trimethylsilylimidazole, are also known and described e.g. in Angew. Chemie 1965, page 424. Other compounds can be easily prepared by the same methods.

On account of tautomeric structures in the starting materials of the formula III, certain unsymmetrically substituted azoles such as pyrazole, 1,2,3-triazole, 1,2,4-triazole etc., exist in the form of two isomers. Pyrazole, for example, has the forms

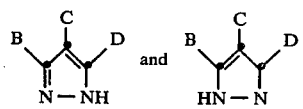 and so that the compounds of the formula I in these two cases also exist in the form of two isomers, the relationship of which is determined by the nature of the radicals B, C and D and can influence the herbicidal properties.

The following Examples describe methods of obtaining the compounds of the invention. Other compounds of the formula I obtained are tabulated after the Examples.

EXAMPLE 1

17.3 g (0.05 mole) of α-[4-(3',5'-dichloropyridyl-2'-oxy)-phenoxy]propionyl chloride are added dropwise at 10° C. to a solution of 7 g (0.05 mole) of 1-trimethylsilylpyrazole in 30 ml of toluene, whereupon the temperature rises to 30° C. No more starting material is present after 15 minutes. The reaction mixture is concentrated in a rotary evaporator at 55° C. and then dried in a high vacuum, affording an oil which crystallises on trituration with petroleum ether. Yield: 15.9 g (84.1%) of α-[4-(3',5'-dichloropyridyl-2'-oxy)-phenoxy] propion-1-yl-pyrazole with a melting point of 104°–106° C. and having the formula

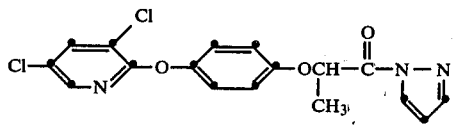

EXAMPLE 2

17.3 g (0.05 mole) of α-[4-(3',5'-dichloropyridyl2-oxy)-phenoxy]propionyl chloride are added dropwise at 10° C. to a solution of 7.1 g (0.05 mole) of 1-trimethylsilyl-1,2,4-triazole in 30 ml of toluene, whereupon the temperature rises slowly to 29° C. No more starting material is present after 15 minutes. The reaction mixture is concentrated in a rotary evaporator at 55° C. and dried in a high vacuum, affording 18.1 g (95.8%) of α-[4-(3',5'-dichloropyridyl-2-oxy)-phenoxy]propion-1-yl-1,2,4-triazole with a refractive index of $n_D^{23}$ 1.5838 and having the formula

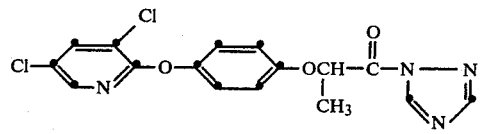

EXAMPLE 3

17.3 g (0.05 mole) of α-[4-(3',5'-dichloropyridyl-2'-oxy)-phenoxy]propionyl chloride are added dropwise at 80° C. to a solution of 7 g (0.05 mole) of 1-trimethylsilylimidazole in 30 ml of toluene, whereupon the temperature rises to 87° C. No more starting material is present after 30 minutes in a hot bath. The reaction mixture is concentrated in a rotary evaporator and the residual oil dried in a high vacuum, yielding 16.8 g (88.9% of theory) of α-[4-(3',5'-dichloropyridyl-2'-oxy)-phenoxy]propion-1-yl-imidazole with a refractive index of $n_D^{23}$ 1.5763 and having the formula

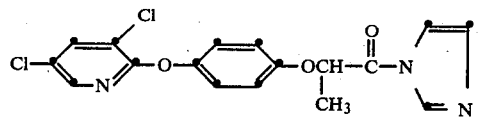

The following compounds of the formula I were also obtained.

| Example | Z | A | Physical data |
|---|---|---|---|
| 4 | 4-trifluoromethylphenyl | pyrazol-1-yl | |
| 5 | 4-trifluoromethylphenyl | imidazol-1-yl | |
| 6 | 4-trifluoromethylphenyl | 1,2,4-triazol-1-yl | |
| 7 | 3-chloro-5-trifluoromethylpyrid-(2)-yl | pyrazol-1-yl | m.p. 70–72° C. |
| 8 | 3-chloro-5-trifluoromethylpyrid-(2)-yl | imidazol-1-yl | |
| 9 | 3-chloro-5-trifluoromethylpyrid-(2)-yl | 1,2,4-triazol-1-yl | m.p. 72–74° C. |
| 10 | 3-chloro-5-trifluoromethylpyrid-(2)-yl | 3,5-dimethylpyrazol-1-yl | m.p. 118–120° C. |

Even when used in low rates of application, the α-phenoxypropionylazoles of the formula I and compositions containing them possess an excellent selective herbicidal action against monocotyledonous weeds in different crops, preferably in crops of dicots. A preferred field of use is e.g. the control of species of gramineous weeds in crops such as cotton, sugar beet, soybeans and vegetables, and also in wheat.

Although the compounds of the formula I are very effective in both pre- and postemergence application, their use as contact herbicides in postemergence application would seem to merit preference. However, the preemergence application of the compounds, especially those containing trifluoromethyl substituents, is also of interest.

The compounds (active ingredients) of the formula I are formulated as e.g. 25% wettable powders or 20% emulsifiable concentrates and, diluted with water, are applied postemergence to the crops.

HERBICIDAL ACTION ON POSTEMERGENCE APPLICATION

Different cultivated plants and weeds are reared from seeds, in pots, in a greenhouse until they have reached the 4- to 6-leaf stage. The plants are then sprayed with aqueous active ingredient emulsions in 3 different concentrations (0.5, 0.25 and 0.125 kg/ha). The treated plants are then kept under optimum conditions of light, watering, temperature (22°–25° C.) and humidity (50–70% relative humidity). The test is evaluated after 15 days in accordance with the following rating:

1 = plants have withered
2 = 8 = intermediate stages of damage
9 = plants as untreated control In this test, the compounds of the invention are compared with the structurally similar α-[4-(3',5'-dichloropyridyl-2'-oxy)phenoxy]propionylamides of N-heterocyclic compounds known from German Offenlegungsschrift No. 2 546 251, Examples 57 and 71, and are found to be more active, as the results reported in the subsequent table show.

RESULTS

Comparison compound A = German Offenlegungsschrift No. 2 546 251, Ex. 71:

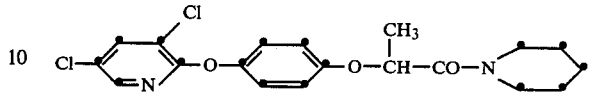

Comparison compound B = German Offenlegungsschrift No. 2 546 251, Ex. 57:

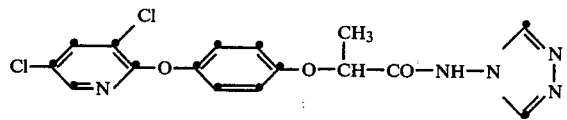

| Compound Example | kg/ha | Cultivated plants | | | | | | | | | Weeds | | | | | | | | | | | | | | | | | | | |
|---|---|---|---|---|---|---|---|---|---|---|---|---|---|---|---|---|---|---|---|---|---|---|---|---|---|---|---|---|---|---|
| | | Wheat | | | Soybeans | | | Sugar beet | | | Avena fatua | | | Lolium | | | Alopecurus | | | Digitaria | | | Echinochloa | | | Sorghum halopense | | | Rottboellia | | |
| | | 0.5 | 0.25 | 0.125 | 0.5 | 0.25 | 0.125 | 0.5 | 0.25 | 0.125 | 0.5 | 0.25 | 0.125 | 0.5 | 0.25 | 0.125 | 0.5 | 0.25 | 0.125 | 0.5 | 0.25 | 0.125 | 0.5 | 0.25 | 0.125 | 0.5 | 0.25 | 0.125 | 0.5 | 0.25 | 0.125 |
| 1 | | 7 | 9 | 9 | 9 | 9 | 9 | 9 | 9 | 9 | 2 | 2 | 4 | 2 | 2 | 3 | 1 | 2 | 2 | 1 | 1 | 2 | 1 | 1 | 1 | 1 | 1 | 2 | 1 | 2 | 2 |
| 2 | | 8 | 9 | 9 | 9 | 9 | 9 | 9 | 9 | 9 | 2 | 2 | 4 | 2 | 2 | 3 | 2 | 2 | 2 | 1 | 2 | 2 | 1 | 1 | 1 | 1 | 1 | 3 | 1 | 1 | 1 |
| 3 | | 8 | 9 | 9 | 9 | 9 | 9 | 9 | 9 | 9 | 1 | 2 | 2 | 2 | 2 | 2 | 1 | 2 | 3 | 1 | 1 | 1 | 1 | 1 | 1 | 1 | 1 | 1 | 1 | 1 | 2 |
| A | | 9 | 9 | 9 | 9 | 9 | 9 | 9 | 9 | 9 | 2 | 3 | 9 | 4 | 8 | 9 | 2 | 3 | 3 | 2 | 3 | 9 | 1 | 1 | 8 | 2 | 4 | 9 | 2 | 6 | 8 |
| B | | 9 | 9 | 9 | 9 | 9 | 9 | 9 | 9 | 9 | 2 | 7 | 9 | 3 | 4 | 8 | 2 | 7 | 9 | 2 | 2 | 3 | 1 | 1 | 6 | 3 | 6 | 9 | 1 | 7 | 8 |

The active ingredients (compounds) of the formula I are stable compounds which are soluble in conventional organic solvents, such as alcohols, ethers, ketones, dimethyl formamide, dimethyl sulfoxide etc.

The invention also relates to herbicidal compositions which contain the compounds of the formula I as active component.

The compositions of the present invention are obtained in known manner by intimately mixing and grinding active ingredients of the general formula I with suitable carriers and/or adjuvants, with or without the addition of antifoams, wetting agents, dispersants and/or solvents which are inert to the active ingredients. The active ingredients can be processed to the following formulations:

solid formulations: dusts, tracking powders, granules (coated granules, impregnated granules and homogeneous granules);

active ingredient concentrates which are dispersible in water: wettable powders, pastes, emulsions, emulsifiable concentrates;

liquid formulations: solutions.

The concentrations of active ingredient in the compositions of this invention are between 1 and 80 percent by weight. As circumstances may require, the active ingredients can also be applied in low concentrations of about 0.05 to 1 percent by weight.

The following Examples will serve to illustrate in more detail the preparation of solid and liquid formulations containing the compounds of the invention. Throughout, parts and percentages are by weight.

EMULSIFIABLE CONCENTRATE

The following ingredients are mixed to formulate a 25% emulsifiable concentrate:

25 parts of a compound of the formula I,
5 parts of a mixture of nonylphenolpolyoxyethylene and calcium dodecylbenzenesulfonate,
15 parts of cyclohexanone,
55 parts of xylene.

This concentrate can be diluted with water to give emulsions in suitable concentrations of e.g. 0.1 to 10%. Such emulsions are suitable for controlling weeds in crops of cultivated plants.

GRANULES

The following substances are used to formulate 5% granules:

5 parts of the compound of Example 7,
0.25 part of epoxidised vegetable oil,
0.25 part of cetyl polyglycol ether
3.50 parts of polyethylene glycol,
91 parts of kaolin (particle size 0.3–0.8 mm).

The active ingredient is mixed with epoxidised vegetable oil and the mixture is dissolved in 6 parts of acetone; the polyethylene glycol and cetyl polyglycol ether are then added. The resultant solution is sprayed on kaolin, and the acetone is subsequently evaporated in vacuo.

WETTABLE POWDER

The following constituents are used to formulate (a) a 70% and (b) a 10% wettable powder:

(a)

70 parts of the compound of Example 3,
5 parts of sodium dibutylnaphthylsulfonate,
3 parts of naphthalenesulfonic acid/phenolsulfonic acid/formaldehyde condensate (3:2:1),
10 parts of kaolin,
12 parts of Champagne chalk;

(b)

10 parts of the compound of Example 2,
3 parts of a mixture of the sodium salts of saturated fatty alcohol sulfates,
5 parts of naphthalenesulfonic acid/formaldehyde condensate,
83 parts of kaolin.

The respective active ingredient is applied to the corresponding carriers (kaolin and chalk) and then these are mixed and ground, to yield wettable powders of excellent wettability and suspension power. By diluting these wettable powders with water it is possible to obtain suspensions containing 0.1 to 80% of active ingredient. These suspensions are suitable for controlling weeds in cultivations of plants.

PASTE

The following substances are used to formulate a 45% paste:

45 parts of the compound of Example 10,
5 parts of sodium aluminium silicate,
14 parts of cetyl polyglycol ether with 8 moles of ethylene oxide,
1 parts of oleyl polyglycol ether with 5 moles of ethylene oxide,
2 parts of spindle oil,
10 parts of polyethylene glycol,
23 parts of water.

The active ingredient is intimately mixed with the additives in appropriate devices and ground. By diluting the resultant paste with water, it is possibe to prepare suspensions of the desired concentration.

What is claimed is:

1. An α-phenoxypropionylazole of the formula I

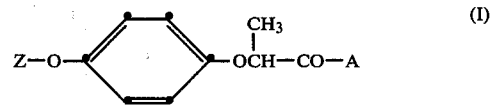

wherein X is 3,5-dichloropyrid-(2)-yl or 3-chloro-5-trifluoromethyl-pyrid-(2)-yl, and A is an polyazole radical which is bonded through a ring nitrogen atom and which can be substituted by one or more of halogen, alkyl, alkoxy, alkylthio or perfluoroalkyl, each containing at most 4 carbon atoms, by cyano, carboxyl, and carbalkoxy containing at most 4 carbon atoms in the alkoxy moiety, or by $C_1$-$C_4$alkanoyl, and A can also denote a salt of a diazole or a triazole.

2. An α-phenoxypropionylazole according to claim 1, wherein Z is 3,5-dichloropyrid-(2)-yl.

3. An α-phenoxypropionylazole according to claim 1, wherein Z is 3-chloro-5-trifluoromethyl-pyrid-(2)-yl.

4. An α-phenoxypropionylazole according to claim 1, wherein A is pyrazol-1-yl, imidazol-1-yl, 1,2,4-triazol-1-yl or 3,5-dimethylpyrazol-1-yl.

5. α-[4-(3',5'-Dichloropyridyl-2'-oxy)-phenoxy]propion-1-yl-pyrazole according to claim 2.

6. α-[4-(3',5'-Dichloropyridyl-2'-oxy)-phenoxy]propion-1-yl-1,2,4-triazole according to claim 2.

7. α-[4-(3',5'-Dichloropyridyl-2'-oxy)-phenoxy]propion-1-yl-imidazole according to claim 2.

8. A herbicidal composition containing a herbicidally effective amount of an α-phenoxypropionylazole of the formula I according to claim 1, together with an inert liquid or solid diluent or adjuvant.

9. A herbicidal composition according to claim 8 which contains a herbicidally effective amount of a compound α-[4-(3',5'-dichloropyridyl-2'-oxy)-phenoxy]propion-1-yl-pyrazole, α-[4-(3',5'-dichloropyridyl-2'-oxy)-phenoxy]propion-1-yl-1,2,4-triazole and α-[4-(3',5'-dichloropyridyl-2'-oxy)-phenoxy]propion-1-yl-imidazole.

10. A method of selectively controlling monocotyledonous weeds in crops of cultivated plants which method comprises applying thereto a herbicidally effective amount of an α-phenoxypropionylazole according to claim 1.

11. A method according to claim 10 in which the cultivated plants are dicotyledonous plants.

12. A method according to claim 11 in which, in the compound, Z is 3,5-dichloropyrid-(2)-yl or 3-chloro-5-trifluoromethyl-pyrid-(2)-yl.

13. A method according to claim 12 in which, in the compound, A is pyrazole-1-yl, imidazol-1-yl, 1,2,4-triazol-1-yl or 3,5-dimethylpyrazol-1-yl.

14. The method according to claim 13 in which the compound is α-[4-(3',5'-dichloropyridyl-2'-oxy)phenoxy]propion-1-yl-pyrazole.

15. The method according to claim 13 in which the compound is α-[4-(3',5'-dichloropyridyl-2'-oxy)-phenoxy]propion-1-yl-1,2,4-triazole.

16. The method according to claim 13 in which the compound is α-[4-(3',5'-dichloropyridyl-2'-oxy)-phenoxy]propion-1-yl-imidazole.

17. A method according to claim 11 in which the cultivated plant is wheat, cotton, sugar beet, soybeans or vegetables.

* * * * *

UNITED STATES PATENT AND TRADEMARK OFFICE
CERTIFICATE OF CORRECTION

PATENT NO. : 4,311,513
DATED : JANUARY 19, 1982
INVENTOR(S) : BEAT BOHNER ET AL

It is certified that error appears in the above—identified patent and that said Letters Patent is hereby corrected as shown below:

Claim 1, Column 10, line 47 reads:

"wherein X is 3,5-dichloropyrid-(2)-yl or 3-chloro-5-tri-"

Should read:

-- wherein Z is 3,5-dichloropyrid-(2)-yl or 3-chloro-5-tri- --

Signed and Sealed this

Sixth Day of April 1982

|SEAL|

*Attest:*

*Attesting Officer*

GERALD J. MOSSINGHOFF
*Commissioner of Patents and Trademarks*